US010857572B2

(12) United States Patent
Lyon

(10) Patent No.: US 10,857,572 B2
(45) Date of Patent: Dec. 8, 2020

(54) APPARATUS TO CONTROL REACTION OF PEROXIDE AND ALKALINE

(71) Applicant: William M Lyon, Marietta, GA (US)

(72) Inventor: William M Lyon, Marietta, GA (US)

( * ) Notice: Subject to any disclaimer, the term of this patent is extended or adjusted under 35 U.S.C. 154(b) by 0 days.

(21) Appl. No.: 16/530,436

(22) Filed: Aug. 2, 2019

(65) Prior Publication Data

US 2019/0351083 A1 Nov. 21, 2019

Related U.S. Application Data

(63) Continuation-in-part of application No. 15/330,947, filed on Mar. 2, 2016, now Pat. No. 10,426,853.

(51) Int. Cl.
| | |
|---|---|
| *B08B 3/08* | (2006.01) |
| *B08B 3/02* | (2006.01) |
| *A61L 2/18* | (2006.01) |
| *A61L 2/24* | (2006.01) |

(52) U.S. Cl.
CPC .............. *B08B 3/026* (2013.01); *A61L 2/186* (2013.01); *A61L 2/24* (2013.01); *A61L 2202/15* (2013.01)

(58) Field of Classification Search
None
See application file for complete search history.

(56) References Cited

U.S. PATENT DOCUMENTS

| | | | | | |
|---|---|---|---|---|---|
| 4,436,113 | A | * | 3/1984 | Finger .................. | B01F 5/0413 134/100.1 |
| 4,540,445 | A | * | 9/1985 | Burns, Jr. .............. | B41F 35/00 101/424 |
| 5,830,836 | A | * | 11/1998 | Smith ..................... | C09D 9/00 510/212 |
| 8,807,158 | B2 | | 8/2014 | Harris | |
| 2008/0280537 | A1 | * | 11/2008 | Urban ..................... | B08B 9/00 451/36 |
| 2015/0209835 | A1 | * | 7/2015 | Heuckeroth ........... | B08B 3/026 239/127 |

\* cited by examiner

*Primary Examiner* — Mikhail Kornakov
*Assistant Examiner* — Ryan L. Coleman
(74) *Attorney, Agent, or Firm* — Moore, Ingram, Johnson & Steele LLP

(57) ABSTRACT

The present invention relates to an apparatus designed to control the application of the previously uncontrollable reaction of a peroxide composition and an alkaline composition, and accurately maintain the desired composition ratios for removal of and destruction of microbiological and organic contamination on a surface safely and without waste of the materials. The apparatus may also be used to maintain the highest demulsifying and antimicrobial activity of an organic acid composition blended with a peroxide composition by limiting contact time and the level of degradation of the components of the organic acid composition. A method of using the apparatus is provided for removing biofilm, bacteria, fungal cells, spores, fragments, and hyphae, microbiological slime, and organic contaminants from porous and non-porous surfaces, maintaining the integrity and life expectancy of the substrates, and increasing their resistance to new biofilm formation and microbiological deposition.

3 Claims, 2 Drawing Sheets

APPARATUS TO CONTROL REACTION OF PEROXIDE AND ALKALINE

CROSS REFERENCE TO RELATED APPLICATION

The present application is a nonprovisional application is a continuation-in-part of U.S. application Ser. No. 15/330,947, claiming benefit of U.S. Provisional Application No. 62/128,336 filed Mar. 4, 2015, and U.S. Non-Provisional application Ser. No. 15/059,068, filed Mar. 2, 2016. The subject matter of those applications is hereby incorporated in its entirety.

FIELD OF THE INVENTION

The present invention relates to an apparatus and method of use for the dual application of a peroxide composition and alkaline composition and/or an organic acid composition for the removal of and destruction of microbiological and organic contamination on a surface safely and without contamination.

BACKGROUND

The present invention relates to a method and apparatus for removing biofilm, bacteria, fungal cells, spores, fragments, and hyphae, microbiological slime, and organic contaminants from porous and non-porous surfaces, maintaining the integrity and life expectancy of the substrates, and increasing their resistance to formation of new biofilm and microbiological deposits. The present invention further relates to a method and device that includes modification of cellulosic and non-cellulosic materials to increase the negative electrostatic potential of their surfaces to resist microbial and organic contaminant attachment and growth into biofilms and deposits. It also relates to a method to safely and economically create, control, and apply a blend of a peroxide composition and an alkaline composition in specialized equipment as a highly aggressive antimicrobial and organic contaminant destroyer in a super-activated solution known by those skilled in the art to normally cause extreme hazards including volatility, pressure and temperature buildup, and explosiveness, as well as to lead to wasteful use of the compositions and blends due to rapid breakdown of the peroxide composition, its super-activated blends, and its more active byproducts. It further relates to a method to maintain the highest demulsifying and antimicrobial activity of an organic acid composition blended with a peroxide composition by dual feed of the separate compositions through specialized equipment designed to limit contact time and level of degradation of the optimum components of the organic acid composition.

Damage from floods and storms such as hurricanes or tornadoes, beyond causing catastrophic destruction of buildings and structures, leaves behind heavy contamination including mud, dirt, debris, and microorganisms such as mold and yeast (fungi), and bacteria. Additionally, water damage caused by leaking and broken pipes and condensation can create environments where contamination by similar microorganisms can allow them to reproduce, thrive, and cause problems. Remediation and restoration of contaminated buildings and structures often involve substantial manual removal efforts such as wiping, scraping, and mopping, but both organic materials and microorganisms normally invade hard-to-reach areas including cracks and crevices in surfaces such as wood, under carpet pile, beneath flooring and tiles, and behind wall coverings. The residual contamination remaining behind after even careful manual cleaning can lead to ongoing structural degradation such as wood rot, air contamination that can cause severe health issues such as from allergies, and horrible odors that make working or living in contaminated structures very difficult or even impossible.

Fungi (yeast and mold) are recognized by medical and veterinary experts as causing a very broad spectrum of health issues in both people and animals. Severe allergies lead to year-round challenges including nasal stuffiness, coughing, eye irritation, skin irritation, breathing problems, accelerated or irregular heartbeats, asthma, and even pneumonitis. More severe problems can occur with infections such as kidney and liver failure, and worsening of other disease conditions such as with cystic fibrosis. Mycotoxins produced by fungi can cause illnesses, weakened immune systems, poisonings, and even death; even though relatively rare, Stachybotrys has been recognized for its threat as the "toxic black mold". Even "sick building syndrome" is now being identified as probably associated with residual mold contamination.

Bacteria can also contaminate buildings and structures after storm, flood, and water damage. Even though requiring a higher level of water for survival, degradative and pathogenic bacteria can find harbors of sufficient moisture in microenvironments where they can continue to survive, especially where substrates maintain residual moisture, organic contaminants have built up, or in areas where dehumidification efforts are less efficient. Diseases such as leptospirosis, cholera, typhoid, and hepatitis, especially where gray water from household contamination or black waters from sewage and sanitation occur, can be initiated by contact with damp surfaces or by inhalation of moisture or bacterial spores during the drying process.

In addition to causing disease and health issues, remaining colonies of fungi and bacteria can cause structural damage including rotting of cellulosic materials and corrosion of metals and other materials of construction. Wood rot organisms utilize cellulose as a foundation, source of moisture, and location for organic food sources. Insufficient or inconsistent dehumidification allows degradation of the structural integrity of wood and wood-containing materials, as well as maintaining environments where pests such as termites can feed and thrive.

Remaining biofilm and biodeposits can lead to corrosive destruction of surfaces including metals such as carbon steel, stainless steel, aluminum, copper, and brass, and non-metals including concrete, polymers and polymer composites, and plastics. Aerobic bacteria within biofilms and deposits establish differential aeration cells that lead to pitting corrosion damage and premature failures. Additionally, anaerobic bacteria such as sulfate-reducers can greatly increase the speed of microbiological pitting where they find protective havens underneath microbiological and organic deposits. Even materials normally resistant to microbiological corrosion and degradation can be damaged by microorganisms thriving on adjacent materials such as wood that are better recognized for their supporting environment. Residual organic fouling and microbiological growth can lead to structural damage and health issues many years after the initial contamination.

Current cleanup efforts focus on diminishing moisture content, which does help reduce the extent of bacterial and fungal threat and damage. However, there is more than enough residual moisture and condensation to support microbiological growth. Fungi (yeasts and molds) can survive on the exterior surfaces and roofs of buildings and structures with only the limited moisture from the environment and the building materials themselves. Where contamination has already occurred such as during floods and storms, residual moisture from just high humidity and elevated temperatures can leave wood components susceptible to rotting organisms. Micro-colonies can also survive until sufficient condensation occurs to reactivate the organisms and lead to thriving communities that threaten the people that inhabit and work in these buildings, their pets, and even the structures themselves.

To reduce or prevent concerns, simple surface cleaning and disinfection must be enhanced by improved attack, destruction, and removal of the microbiological and organic contaminants.

Existing treatments include application of both oxidizing and non-oxidizing biocides. With the concerns of potential human and pet exposure, much of the post-contamination efforts focus on use of oxidizing compounds such as chlorine and/or bromine and non-chlorine peroxide compounds. Chlorine and its other related compounds including hypochlorite and chlorine dioxide have application concerns due to direct chemical attack of materials, along with newer issues over creation of hazardous and potentially carcinogenic byproducts. Therefore, as byproducts of peroxide compounds are simply non-toxic oxygen and water and do not threaten creation of hazardous byproducts and are less prone to structural degradation, they have grown in usage for cleanup and remediation efforts.

Peroxide compounds including hydrogen peroxide, percarboxylic acid, perboric acid, persulfuric acid, metal salts of these compounds, and other peroxide and peroxide-releasing compounds have been used with moderate success. Their ability to penetrate and remove contamination is enhanced by inclusion of surfactants, while the products' resistance to decomposition has been improved by use of stabilizers. However, the antimicrobial efficacy and chemical reactivity of the peroxide compounds is still often insufficient to address all the contamination They rapidly degrade to their inactive byproducts especially in the presence of heavy organic fouling and metals and metal ions including iron, manganese, copper, silver, platinum, and titanium, and they are rapidly broken down to inactive molecules by enzymes including catalase, peroxidase, and other less common ones normally present in all of the targeted microorganisms. The anti-peroxide reaction rate for catalase has been reported as high as 5,000,000 molecules destroyed per enzyme molecule per second, making sufficient treatment by, for example, 8% hydrogen peroxide, almost impossible to achieve; in the presence of substantial microbial populations and/or substantial organic contaminant presence, the hydrogen peroxide is inactivated faster than it can reach the targeted surfaces. Even with very little organic fouling present, peroxide compounds, without the super-activation of the current invention, at or below 8% concentration, are typically broken down to inactive compounds faster than they can accomplish their targeted tasks of killing microorganisms, destroying organic contaminants, and lightening stains.

Hydrogen peroxide is well-recognized for its use to kill bacteria, fungi, viruses, and other microorganisms, and it also is inherently a vital part of all cell metabolism including destruction of internal cell toxins. With external application targeting microorganisms, it offers an extremely broad spectrum of effect including attack of critical cell components such as lipids, proteins, DNA, sulfhydryl groups, and organic compound unsaturation. However, as the cells both produce and are attacked by hydrogen peroxide, there are natural processes that operate to limit the lifetime of and turn off the destructive capability of excess hydrogen peroxide. The primary defense for cells to limit the danger of hydrogen peroxide is through enzymes including catalases and peroxidases. Lower concentration and limited contact by peroxide serve to activate these defense mechanisms, and, therefore, hydrogen peroxide has been historically much less beneficial an antimicrobial than desired.

Acids are known to alter the physical structure of enzymes such as catalase to inactivate their anti-peroxide activity, but recognition by the cells of increased peroxide presence leads to an expanded response by them. The acid-inactivation of enzymes is a reversible reaction, and the increase in, for example, catalase concentration can rapidly turn a seemingly effective peroxide treatment level into an insufficient residual. Some organic acids are able to stabilize the enzyme deformation and prolong the peroxide residual presence, but this improvement still has a limited life.

Additionally, some bacteria respond to chemical threats including peroxide attack by formation of protective spores. Even though this does not create bacterial strains specifically resistant to hydrogen peroxide, it makes killing the organisms much more challenging. Even with extremely high concentrations of peroxide, an antimicrobial treatment by hydrogen peroxide on its own can prove ineffective.

To better address the level of contamination and the need for a higher activity of cleaning and remediation products, alkaline materials have sometimes been used to enhance the peroxide compositions through development of free radicals. In alkaline conditions, hydrogen peroxide initially forms perhydroxyl anions ($HOO^-$), also referred to as hydroperoxide anions, which are strong nucleophiles. Perhydroxyl anions, though, are not very stable in aqueous solutions, and they rapidly convert to a wide variety of very reactive free radicals including perhydroxyl ($HOO•$), hydroxyl ($•OH$), superoxide anion ($•O_2^-$), and oxyl anion ($•O^-$). The enhanced activity of these alkaline initiated radicals against microbial and organic contaminants, in spite of the rapid rate of peroxide activation, has been of limited practical value, as these structures rapidly break down to non-reactive species and have extremely short life, leading to poor efficiency, product over-application, and substantial waste as the degraded compounds become ineffective.

Levels of degradation of the base peroxide compositions, their alkaline-activated blends, and their reactive species including free radicals, change severely with variables including concentrations of metal and organic contaminants in the compositions, time, pressure, temperature, and pH. Therefore, actual field applications of peroxide compounds at elevated pH's have historically been inefficient, inconsistent, and undependable. To provide beneficial effect with these type chemistries, applications must offer consistent, dependable, economical, and thorough coverage. This beneficial effect can not be achieved with historic application equipment, as ratios of the blends were not maintained as optimized, the rate of degradation was excessive, and degradation rates did not leave sufficient activity to produce the targeted results. New application equipment design is a prerequisite to producing much more predictable and consistent composition blends that would not allow overly sufficient contact during which such degradation could occur.

Application of technologies based on peroxide and alkali combination through a dual and simultaneous feed has not been commercially viable. The mixture of the peroxide and alkaline compositions creates an extremely violent, exothermic and explosive reactions with release of substantial heat and flammable oxygen that literally threatens the lives of application personnel. Heat and pressure buildup are known to cause runaway degradation and explosive reactions, especially when triggered by even minimal contamination from metals or organic compounds, that can damage feed lines, chemical containers, and mixing systems, as well as lead to injuries and chemical exposure. Attempts to use lower concentration peroxide compounds such as less than 8% hydrogen peroxide can slightly reduce the threat, but they are not sufficiently active to accomplish the targeted application needs on their own.

In some historic efforts, the organic contaminant removal and antimicrobial efficacy of a peroxide composition has been enhanced by blending into the formulation at least one organic acid. Some medium length ($C_5$-$C_{12}$), straight chain, fully saturated, carboxylic acids add their own antimicrobial activity to that of the peroxide composition through disruption of microbial cell wall components. Additionally, the activity of these organic acids as surface active agents helps improve penetration and disruption of surface fouling by organic compounds. Further, these acid compounds help distort the physical structure of enzymes including catalase that destroy peroxide compounds such as hydrogen peroxide at unbelievably rapid rates, at least temporarily inactivating the enzymes and allowing much of the peroxide compositions to survive and achieve their targeted benefits in removal and destruction of microbial and organic contaminants However, peroxide compositions, especially in acid environments below about pH 6 where the acid serves to activate the peroxide components to stronger oxidizers, will destroy both the targeted organic and microbial contaminants as well as the organic acids, themselves. Each oxidation by these activated compounds of the organic acids causes them to lose a carbon dioxide molecule during every reaction, creating new organic carboxylic acids that are one carbon length shorter than the originals.

Various chain length organic acids have been extensively evaluated for their antimicrobial efficacy and their surfactant capabilities, and optimum treatment in cleaning and disinfection was targeted by selection of specific organic acids. In spite of this, though, oxidative degradation by peroxide compositions of the chosen organic acids worsened by factors including increasing time, temperature, and pressure, results in a less than optimum group of organic acids that creates inefficient applications, requirements for wasteful overfeed, and inconsistent treatment that leaves voids and openings for rapid failure of restoration and remediation.

As an example, caprylic acid ($C_8$) offers better demulsification and higher antimicrobial efficacy than heptanoic acid ($C_7$) and would optionally be chosen over heptanoic acid to activate and improve the application of a peroxide composition. Improved demulsification from selection of an organic acid such as caprylic can help break emulsified organic materials at the targeted surfaces such as metals to enhance their removal, but it is of even more value when water is being recycled or recirculated for reuse; with allowance of some time for separation, inclusion of an effective demulsifier allows the mechanically entrapped organic compounds to phase separate from the water for easier removal by methods including skimming. Further, demulsifiers allow effective surfactant activity with lower foaming tendency, allowing for lower foam applications where they are desirable, such as with use under high pressure. Additionally, especially where mold remediation is the target of an application, the enhanced antifungal activity of caprylic acid over heptanoic acid would produce more effective results. However, oxidative degradation of the organic acid by the peroxide compounds rapidly changes the original organic acid components from their original chemistry and concentrations. Even with only a limited extension of contact time between the peroxide composition and the organic acid composition in standard pump-up sprayers or pressure washers, a large percentage of the caprylic acid would be oxidized to the much less effective heptanoic acid. Also, in single product formulations with both peroxide component and organic acid components, extended warehouse storage product could, even though the effects might not be visibly or physically observable, greatly reduce the cleaning and antimicrobial efficacy as compared with more recently manufactured material.

To avoid this potential oxidative degradation that would negatively impact the efforts to remove and destroy organic and microbiogical contamination, it might seem obvious to simply and separately apply a peroxide composition and an organic acid composition to the site of the targeted application. However, optimized and tight control over the ratio between the two compositions, efficient dosing and mixing of each composition, and the amount of contact time prior to application must be maintained to achieve the most efficient, economical, consistent, thorough, and dependable treatment applications. New application equipment designed for a dual and simultaneous composition feed is needed to produce much more predictable and consistent composition blends without leaving excessive contact time or other conditions during which organic acid degradation and resultant inefficiencies could occur.

The specialized application apparatus of the present invention allows for the safe and cost-effective use a dual chemical feed of a peroxide composition and an alkaline composition or a peroxide composition and an organic acid composition to create an enhanced activity blend used to treat targeted surfaces for removal and destruction of microbiological and organic contamination of both porous and non-porous surfaces. Almost immediately after the blending of the two compositions, the mixture is rapidly applied to those surfaces to ensure that the optimum and intended combination is achieved and distributed.

SUMMARY OF INVENTION

The present invention relates to an apparatus designed to control the application of the previously uncontrollable reaction of a peroxide composition and an alkaline composition for removal of and destruction of microbiological and organic contamination on a surface safely and without waste of the materials. Alternatively, a peroxide composition and an organic acid composition may be used. For clarity purposes, the term compositions refers to the peroxide composition, the alkaline composition and the organic acid composition and the term blends refers to the peroxide composition in combination with alkaline composition (peroxide/alkaline) and the peroxide composition in combination with the organic acid composition (peroxide/organic acid).

In a preferred embodiment of the current invention, the apparatus uses a dual chemical feed of a peroxide composition and an alkaline composition to create a highly active treatment to remove and destroy microbiological and organic contamination of both porous and non-porous surfaces. During the blending of the two components, the reaction creates short life hydroperoxide anions, perhydroxyl and hydroxyl radicals, superoxide anions, and oxyl anions that greatly enhance the chemical reactivity and antimicrobial efficacy of the applications. In addition, even though these blends are substantially stronger in their chemical reactivity and antimicrobial efficacy, this enhancement is actually accomplished with lower risk of damage to human and animal skin than occurs with acid enhanced peroxide compositions. Alternatively, when the peroxide composition and organic acid composition are used, the mixture is rapidly applied to affected surfaces after blending to ensure that the intended combination is distributed.

In a preferred embodiment, the target of the removal and destruction of the organic and microbiological contamination is mold remediation of buildings and structures that have experienced problems including storm and/or flood damage, water damage from leaking pipes and fixtures, or condensation.

In one preferred embodiment, the peroxide composition comprises at least one of the following: hydrogen peroxide, percarboxylic acid, perboric acid, persulfuric acid, metal salts of these compounds, and other peroxide and peroxide-releasing compounds, while blends of these may provide enhanced benefits. The peroxide composition may also include surfactants and less than 1% acetic acid. The alkaline composition comprises sodium hydroxide, potassium hydroxide, sodium carbonate, sodium bicarbonate, sodium silicate, and other metal hydroxides, or combinations thereof. Alternatively, when the organic composition is used, it may comprise butyric acid, pentanoic acid, caproic acid, heptanioc acid, caprylic acid, acetic acid, pelargonic acid, capric acid, or undecanoic acid.

In a preferred embodiment, the peroxide compound is 5% to 50% hydrogen peroxide, more preferably 8% to 30% hydrogen peroxide, and most preferably 18% to 22% hydrogen peroxide, creating sufficient application strength to appropriately treat the targeted problems. Lower concentrations of peroxide compounds, especially when unreacted with an alkaline composition, are known to be insufficient to accomplish the intended goals and lead to chemical waste, overtreatment that is both wasteful and hazardous, and reduced cost-efficiency.

When the alkaline composition is added to result in a blend of the dual components with a pH of 6 to 12, more preferably 7 to 11, and most preferably 9 to 10, to optimize the creation of hyperactive perhydroxyl and hydroxyl radicals, superoxide anions, and oxyl anions, while reducing waste and increased hazard that occur with overuse of the compositions or their blends. Also, increasing pH to even higher levels would increase the threat of structural damage to the cellulose in substrates such as wood, wood-containing materials, wood pallets, engineered wood products, and paper.

In a preferred embodiment wherein the organic acid composition is used, the organic acid composition comprises a specific organic acid or a blend of specific organic acids selected as based on the demulsifying capacity of those compounds to improve cleaning of surfaces including metals that are substantially contaminated with surface foulants including oils, waxes, and other organic compounds and based on the antimicrobial efficacy, preferably the antifungal efficacy, against microorganisms, thriving within and on deposits and being protected by their high organic compound contamination.

In a preferred embodiment wherein the organic acid is used, the organic acid composition is blended with the peroxide composition in a ratio between 1:8 to 0.01:20.

In a preferred embodiment wherein the alkaline composition is used, the treated surfaces may be chemically modified by the application of the blend of peroxide composition and alkaline composition to create and enhance electrostatic repulsion of those surfaces to microorganisms and organic contaminants that would otherwise be able to be attracted to and attach to them as biofilm and microbiological deposition. The majority of organic and microbiological contaminants have an anionic character, and converting the treated surfaces to be more anionic and/or electronegative will create a repulsive force that reduces the ability of the contaminants to approach and/or attach themselves to those surfaces. Oxidation of compounds including alcohols, glycols, and various other hydrocarbons to aldehydes and ketones increases electronegativity, whereby those locations have an increased influence from uncharged electron pairs, through creation of carbonyl groups ($C=O$). Further oxidation to carboxylic acids and esters increases electronegativity through creation of carboxyl groups (COOH) under neutral or acid conditions, and increases anionicity through conversion to carboxylates ($COO^-$) under alkaline conditions or where salt formation is favored, whereby the locations offer stronger repulsion by an increased number of negatively charged molecules.

In further embodiments, the removal and destruction of the organic and microbiological contaminants are enhanced by oxidative degradation of the organic foulants and polysaccharides often referred to as microbiological "slime". In biofilm and deposits, these compounds serve as protective shields that reduce the effectiveness of antimicrobial treatments through physical interference. The oxidative cleaving of at least some bonds breaks more complex molecular structures down to compounds that are more easily washed away with simple mechanical action such as from rinsing of surfaces.

In some embodiments, the surfaces comprise cellulose-based materials including wood, wood pallets, paper, wallpaper, gypsum wallboard, ceiling tiles, engineered wood products, and wood composites, and metals including carbon steels and stainless steels, concrete, plastics, polymers, and composites. Adjacent materials that may be less susceptible to fouling and attack by organic and microbiological contaminants such as concrete, metals, gypsum, polymers, plastics, and composites may also be protected due to elimination of the nearby potentially high contaminant concentration that could, under other circumstances, lead to a spillover of deposition from the initially fouled and less resistant materials.

In a preferred embodiment, the targeted biofilm and microbiological deposition comprise single-cell bacteria, filamentous bacteria, mold, yeast, algae, and their trapped organic and inorganic contaminants.

In further embodiments, the antimicrobial efficacy of the blends or compositions may be enhanced by inclusion with additional pesticidal compounds including but not limited to zeolites, zinc compounds, diiodomethyl-p-tolylsulfone, 3-iodopropynylbutylcarbamate, 2-(thiocyanomethylthio) benzothiozole, thiabendazole, chlorothalonil, sodium and zinc pyrithiones, boric acid, metaborates, silver and silver compositions, and mixtures thereof.

Further embodiments may optionally include in the compositions, or their subsequent blends: wetting agents, surfactants, and degreasers to better penetrate, clean, and remove contaminants; foaming agents to better lift contaminants out of cracks, crevices, and other areas where contact by mechanical efforts such as wiping, scraping, and mopping are ineffective; corrosion inhibitors to reduce damage to susceptible surfaces such as metals, concrete, polymers, and plastics; carboxylic acids to enhance penetration and efficacy of the blended compositions; additional bleaching agents to address staining; fragrances to reduce contaminant odors and improve the post-treatment environments; and chelants to better remove inorganic contaminants that may be trapped within the microbiological and organic deposition or created during structural corrosion and degradation.

In further embodiment, a thickener may be added to any or all of the compositions or their subsequent blends to improve surface cling, reduce required fluid volume, prolong contact time, and improve exposure and consistent coverage of the treated surfaces.

In another embodiment, any or all of the compositions or their subsequent blends may optionally include an indicator therein selected from the group of dyes, tints, pigments, and ultraviolet light indicators to enable better monitoring of the areas treated, areas missed in treatment, or areas covered by a resulting foam.

In a further embodiment, the application may be followed by treatment with a long-term surface protection to maintain the quality of the treated surface, which would subsequently be exposed to fouling, staining, and degradation conditions.

In another embodiment, the application may be preceded, followed, or combined with cleaning compounds such as a tile and grout cleaner to address specific fouling and contamination issues.

In a preferred embodiment, the application of either of the blended compositions is accomplished in a dip tank with optional overflow that would allow a consistent concentration of active components, in treatment in a countercurrent process water flow, with a spray or in a spray cabinet, with a mist, or by electrostatic spray. The peroxide composition and alkaline composition or the peroxide composition and organic acid composition may be added as separate components blended as a dual feed immediately prior to application in a bath, or with in-line mixing for spray immediately prior to application, or with use of dual sprays at the immediate points of application.

In a preferred embodiment, the dual component feed is accomplished through use of equipment specially designed to meet the challenging requirements for consistent dosage, aggressive attack on materials of construction, and rigorous operating conditions. Optionally, a container or vessel, with or without internal baffles, and/or in-line mixers may be used to enhance mixing of the dual components immediately prior to application.

Materials of construction for the apparatus of the present invention are selected for their resistance to and non-reactivity by the compositions and their resulting blends. In a preferred embodiment, the application equipment has all wetted metal surfaces of stainless steel, Viton and/or Teflon seals and gaskets, and flexible tubing of fluorinated polymer material. However, it is understood that any material that resists and does not react with the compositions may be used.

The apparatus of the present invention may be stationary or portable. In a preferred embodiment, the control panel, which is designed for easy removal for repair or replacement, may be mounted on a portable, two-wheel, aluminum dolly with a built-in step climber for easy movement in and out of maintenance vehicles, up and down stairs, etc., or wall mounted for permanent installation.

The hazardous risk of the substantial heat and pressure generated by the reaction of the peroxide composition and alkaline composition is limited by using just a sufficient amount of reactants to prepare only the specific volume of blended mix at the moment of application. This is accomplished with automatic feedback to immediately start and stop chemical feed with the initiation and cessation of application at the feedpoint through use of methods such as radio remote control, check valves and solenoid valves. This prevents buildup of reactive components, blend of compositions, or byproducts in enclosed vessels, lines, and application equipment that could result in violent, auto-accelerating, and runaway reactions, whereby the rate of heat generation exceeds the rate of heat removal. The temperature of the reaction blends begins to rise, thereby increasing the heat generation rate and forcing an ever-increasing cycle of temperature and pressure buildup over a very short time. Off-side and chain reactions can also be initiated, leading to explosion, destruction of equipment, and severe hazards for personnel.

Similarly, when the peroxide composition is used with the organic acid composition the extent of oxidative degradation of the components from the organic acid composition is limited by using just a sufficient amount of reactants to prepare only the specific volume of blended mix at the moment of application. This is accomplished with automatic feedback to immediately start and stop chemical feed with the initiation and cessation of application at the feedpoint through use of methods such as radio remote control and check valves. This prevents premature blending of the reactive components blending of compositions prior to application needs.

Further, with the enhanced control of the flow rate of both the peroxide and alkaline compositions or peroxide and organic acid compositions in the current invention, the appropriate balance between the two is maintained at optimum, providing the consistency of activity to the application point that is necessary to achieve dependable and efficient results. In an embodiment wherein the peroxide composition is used with the alkaline composition the rate of reaction for the activation of the peroxide composition is increased to an optimum with some increase in pH, most preferably 9-10, with exceeding that level reducing economy, encouraging competing side reactions, and speeding degradation of the compositions, the blends, and the more active radicals. In the embodiment wherein the peroxide composition is used with the organic acid, the level of activation of the peroxide composition is enhanced by blending the organic acid composition with the peroxide composition to a targeted ratio based on the specific application to a controlled ratio between 1:8 to 0.01:20.

Standardly available feed equipment such as pump-up sprayers and pressure washers have been used in attempts to combine feed of peroxide compounds and alkaline compounds into a single application. Pump-up sprayers by their design pressurize contained liquid, not allowing optimization of the compositions blends as well as trapping materials that can produce violent or explosive, runaway reactions. Pressure washers only had standard trigger activation, whereby a trigger at a handheld wand would open or close flow, and the pump would either be running throughout or would stop when a set back pressure at the equipment was exceeded. Even though this type of system could help prevent leakage at the distribution nozzle, it trapped fluid in the equipment and lines between the pump and the distribution nozzle. As the peroxide and alkaline compositions were already mixed, within a short time of contact, peroxide activation would occur and pressure and temperature would begin to rapidly rise, leading to runaway reactions and probable catastrophic destruction from explosion and fire. This threat was critical in prevention of commercial development of peroxide/alkaline applications.

Similar entrapment of reactive components would result from the use of a pump-up sprayer used to combine a peroxide composition and an organic acid composition that could result in conditions hazardous to application personnel. Further, standard pressure washers only had a trigger activation, whereby the trigger at the handheld wand would open or close flow of the blend. The pump would either be running throughout or would stop when a set back pressure at the equipment was exceeded. This type of system helps prevent leakage at the distribution nozzle and unintended spraying of blend, but it can also trap fluids in the equipment and lines between the pump and the distribution nozzle. As the peroxide and organic acid compositions were already mixed, any trapped compositions or their blends would begin to allow degradative oxidation of the organic acids contained within. Further, the delayed shutoff of the pump could allow some hazardous conditions to arise with the increased pressure between it and the distribution nozzle. Therefore, a new equipment design was necessary to achieve a truly optimized commercial application of dual feed peroxide and organic acid compositions.

In a preferred embodiment of the current invention, a pump introducing the compositions (peroxide and alkaline or peroxide and organic acid) from reservoirs and providing mixing is started and stopped at the point of distribution, the dual feed chemical composition reserves are isolated from mixing at the pump suction inlet such as by solenoids and/or check valves. In a preferred embodiment, all previously blended solutions of the two compositions are allowed to "gas off" and release pressure buildup via a check valve immediately prior to a discharge nozzle at the end of the application hose. The pump may be controlled by a standard electrical switch or remote control. In a most preferred embodiment, the remote control is maintained at the point of application and is wireless, such as by radio frequency, with at least one channel to power on and off the pump and optionally additional channels to allow for control of additional functions from the application point. Further, foot valves are optionally installed in the composition reservoirs with the exception of the peroxide composition to prevent drainage of the suction pickup tubes and loss of prime. In a further embodiment, a pulsation dampener may be used.

The introduction of the two compositions can be through a downstream orifice-type injector or into the suction side of a pump, with the pump optionally serving to mix the compositions or optionally having in-line mixers subsequently optimize mixing. In a preferred embodiment, the injector is a Hyrda-Flex Chem-Flex injector as disclosed in U.S. Pat. No. 8,807,158.

In a preferred embodiment, the application equipment includes a positive displacement pump of the type including diaphragm, piston, and centrifugal. The pump volume is preferably 0.1-2.0 gallons per minute (gpm), more preferably 0.1-1.0 gallons per minute, and most preferably 0.3-0.6 gallons per minute with an operating pressure of preferably 0.0-3,000 pounds per square inch (psi), more preferably 0.0-1,000 pounds per square inch, and most preferably 10-120 pounds per square inch.

In a preferred embodiment, a pressure relief valve is installed on the output side of the pump to release any pressure that could occur with unexpected blockage of the application hose or application wand. The pressure relief valve has a discharge cracking pressure of preferably between 500 and 1,000 pounds per square inch, more preferably between 250 and 500 pounds per square inch and most preferably between 125 and 150 pounds per square inch. In this preferred embodiment, the pump pushes the compositions and/or their blends toward the distribution nozzle, and a check valve opens with pressure to allow application of the compositions and/or their blends. With this arrangement, no trigger release to open the nozzle, which could inadvertently cause trapping of the compositions and/or their blends prior to opening, is needed or used. However, a directional application wand may still be included with the capability to start and stop the chemical flow at the application point to prevent unintentional chemical release that could threaten hazards including spraying of personnel or non-targeted surfaces. In a further embodiment, the system may include a system for capturing waste, such as a waste bottle.

In another preferred embodiment, the dual feed compositions are isolated from each other and the mixing region of the application equipment by a system of check valves that help prevent premature blending and excessive reaction time to limit the potential for runaway and self-accelerating reactions and chemical waste due to product degradation with time. Alternatively, electrically-operated, stainless steel solenoid valves may be used. In a preferred embodiment, these solenoid valves are opened with power to the application equipment and selection of the desired application such as with a selector switch, whereby the pumping of the compositions can begin with simple remote activation of the pump from the application point.

In further embodiments, pickup suction tubes may be premounted into composition storage reservoirs to reduce the risk of personnel exposure to the compositions, as well as to reduce the risk for accidental metal or organic compound contamination that could initiate runaway or auto-accelerating reactions. In some more preferred embodiments, specialized connectors that are specific to the type of composition intended for that particular assembly may be preinstalled on the connecting hoses and composition storage reservoirs to prevent incorrect connections to the wrong type of composition and the potentially hazardous reactions that could occur. Alternatively, the suction tubes may be pre-primed with the appropriate composition.

In another preferred embodiment wherein the alkaline composition is used, the metering of the alkaline composition is preferably controlled by a metering device, most preferably as predetermined by an orificed metering device installed in the suction tube of the alkaline composition. The metering device regulates the amount of alkaline composition injected into the peroxide composition flow to achieve a resulting pH of the blend of preferably 6-12, more preferably 7-11, and most preferably 9 to 10. Control of the appropriate ratios of the alkaline composition to the peroxide composition flow is necessary to optimize the activation and ensure a beneficial, economical, and consistent application.

In another preferred embodiment wherein the organic acid composition is used, the metering of the organic acid composition is preferably controlled by a metering device, most preferably as predetermined by an orificed metering device installed in the suction tube of the organic acid composition. The metering device regulates the amount of organic acid composition injected into the peroxide composition flow to achieve a resulting targeted ratio based on the specific application of between 1:8 to 0.01:20. Control of the appropriate ratios of the organic acid composition to the peroxide composition flow is necessary to optimize the activation, reduce waste, and ensure a beneficial, economical, and consistent application.

In still another preferred embodiment, leakage and siphoning of excess compositions or their blends are prevented by use of a check valve immediately prior to a discharge spray nozzle of the application equipment that allows release of any pressure buildup in the lines, application equipment, or directional wand, while closing down to prevent dripping or leaking and potential chemical exposure by non-pressurized liquids. The check valve has a crack pressure of preferably 0.1-100 pounds per square inch, more preferably 0.1-50 pounds per square inch, and most preferably 0.1-5.0 pounds per square inch of pressure. This check valve allows the pump to be turned off for intermittent cycles without excessive pressure build up in the pump, application hose, and application or directional wand as could occur with standard trigger sprayers, yet still allows the operator the convenience of control at the distribution point to start and shut off the application without the dangerous buildup of pressure that would occur with normal trigger stoppage of the pump.

Equipment can be specifically designed by those skilled in the art to provide tighter control of the volumes of blends (for example 0.3 to 0.6 gallons per minute) being applied to the surfaces reducing waste by limiting the volume to just a sufficient amount to only wet the surface, along with optional inclusions such as extended hose to make applications more convenient. Excess flow beyond the amount necessary to only wet the surface contributes to wasted runoff and substantial overuse of the compositions and their blends.

In a preferred embodiment, the application equipment has a selector switch to select an option of the peroxide composition by itself or a combination of the peroxide composition with a metered amount of the alkaline or organic acid composition as a peroxide composition accelerator into the flow of the peroxide.

In some embodiments, the application equipment has the ability to select preferably at least one other chemical source, more preferably two or more other chemical sources, via the operational selection switch. In these embodiments, the application equipment may optionally have a third suction pickup tube that can be used to pump water through the pump, hoses, and wand to clean the wetted components. Alternatively, in some other embodiments, the application equipment can use that third suction pickup tube to apply an additional chemical composition including a long-term antimicrobial, a tile and grout cleaner, a degreaser, a truck wash, or other alkaline or acid chemicals. The application equipment machine may optionally have a fourth suction pickup tube. In some embodiments, the selector switch can cause the application equipment to simultaneously pump a long-term antimicrobial via the third pickup tube and a color indicator, preferably blue, via the fourth pickup tube being metered into the third pickup tube to give the antimicrobial a color to monitor where the antimicrobial has been applied and where voids in even distribution of the antimicrobial may remain.

In some embodiments, treatment with an optional long-term antimicrobial including a color indicator, preferably blue, maintains that color on the treated surfaces for more than 30 days of flowing water intrusion before washing the color from the surface.

The apparatus of the present invention may be stationary or portable.

In a further embodiment, the application equipment uses less than 4 amperes of 115 volt, 50 to 60 cycle current. In some embodiments, the power source incorporates ground fault protection including a ground fault circuit interrupter (GFCI) to reduce the risk for electrical shock.

In another embodiment, the blends are optionally applied at elevated temperatures or under pressure to enhance the efficiency of attack and removal of the contaminants. In other embodiments, heat and/or pressure are applied to the targeted surfaces before, during, or after application of the blends, such as in an autoclave.

In another preferred embodiment, porous and non-porous surfaces may be treated to greatly reduce microbiological contamination, allowing them to be considered sterilized, disinfected, or sanitized.

In an embodiment wherein the alkaline composition is used, the sterilization, disinfection, and sanitization may be performed with application of the peroxide composition at 1 ppm to 10,000 ppm, and the alkaline composition preferably added to result in a blend of the dual components with a pH of 6 to 12, more preferably 7 to 11, and most preferably 9 to 10, to optimize the creation of hyperactive perhydroxyl and hydroxyl radicals, superoxide anions, and oxyl anions, while reducing waste and increased hazard that occurs with overuse. Similarly, in an embodiment wherein the organic acid composition is used, the sterilization, disinfection, and sanitization may be performed with application of the peroxide composition at 1 ppm to 10,000 ppm, and the organic acid composition is preferably added to result in an optimized ratio of the organic acid composition between 1:8 to 0.01:20, while reducing waste and increased risk that occurs with overuse.

In further embodiments, the porous and non-porous surfaces treated to reduce microbiological and organic contaminants are equipment or food contact surfaces in food processing facilities and retail and commercial food preparation areas.

In other embodiments, the treatment to reduce microbiological and organic contaminants will be directly to food and food products including meats, poultry, fruit, and vegetables. In addition to offering enhanced antimicrobial activity and organic compound degradation, the activation of the peroxide composition by an alkaline composition accomplishes this with less risk for decreased quality by accomplishing the targets with less threatened damage to the skin and muscle of meats and poultry, as compared with acid enhanced peroxide compositions.

In another embodiment, the treatment with the peroxide/alkaline blend to reduce microbiological and organic contaminants will be to animal hides and skins, whereby the alkaline activated blend threatens substantially less damage to the hides and skins than peroxide blends enhanced with acids.

In another embodiment, the treatment with the peroxide/alkaline blend to reduce microbiological and organic contaminants will be to human and animal skin and tissue associated with wounds and infections including cuts, scrapes, and punctures and skin disease. Microbes can cause and/or exacerbate infections and disease. In recent years many drug-resistant varieties of pathogenic organisms have made treatment strategies less effective or even obsolete. The antimicrobial effect of the blends of peroxide and alkaline compositions does not target narrow metabolic pathways that can leave openings for other resistant forms with alternate pathways to take hold but offers very broad and destructive attacks that effectively kill an almost limitless spectrum of microorganisms. This is all accomplished with the enhanced activity of the blends that overcome natural defenses of the microorganisms such as catalase enzymes with much less skin and tissue threats normally expected with high concentration peroxide compounds and compositions.

In other preferred embodiment, the application with the peroxide/alkaline blend to reduce microbiological and organic contaminants involves treatment of plants including fruit and produce where the treatment is applied to areas including roots, stems, bark, leaves, and fruits and vegetables to reduce organic and microbial contaminants while offering reduced threat for damage to their cellulosic components. A wide variety of plant disease is associated with microbial contaminants, but many potential treatment options can damage the cellulosic structures that support and strengthen the plant's components. One non-limiting example is to the various components of orange trees and fruit to reduce the damage from "citrus greening", which has led to reduced production of up to 50% and is thought to be caused by bacteria.

In other embodiments, the porous and non-porous surfaces treated n to reduce microbiological and organic contaminants are in cooling water systems, cooling towers, condensers, and wastewater treatment systems.

DETAILED DESCRIPTION OF THE EMBODIMENTS

Figure 1:
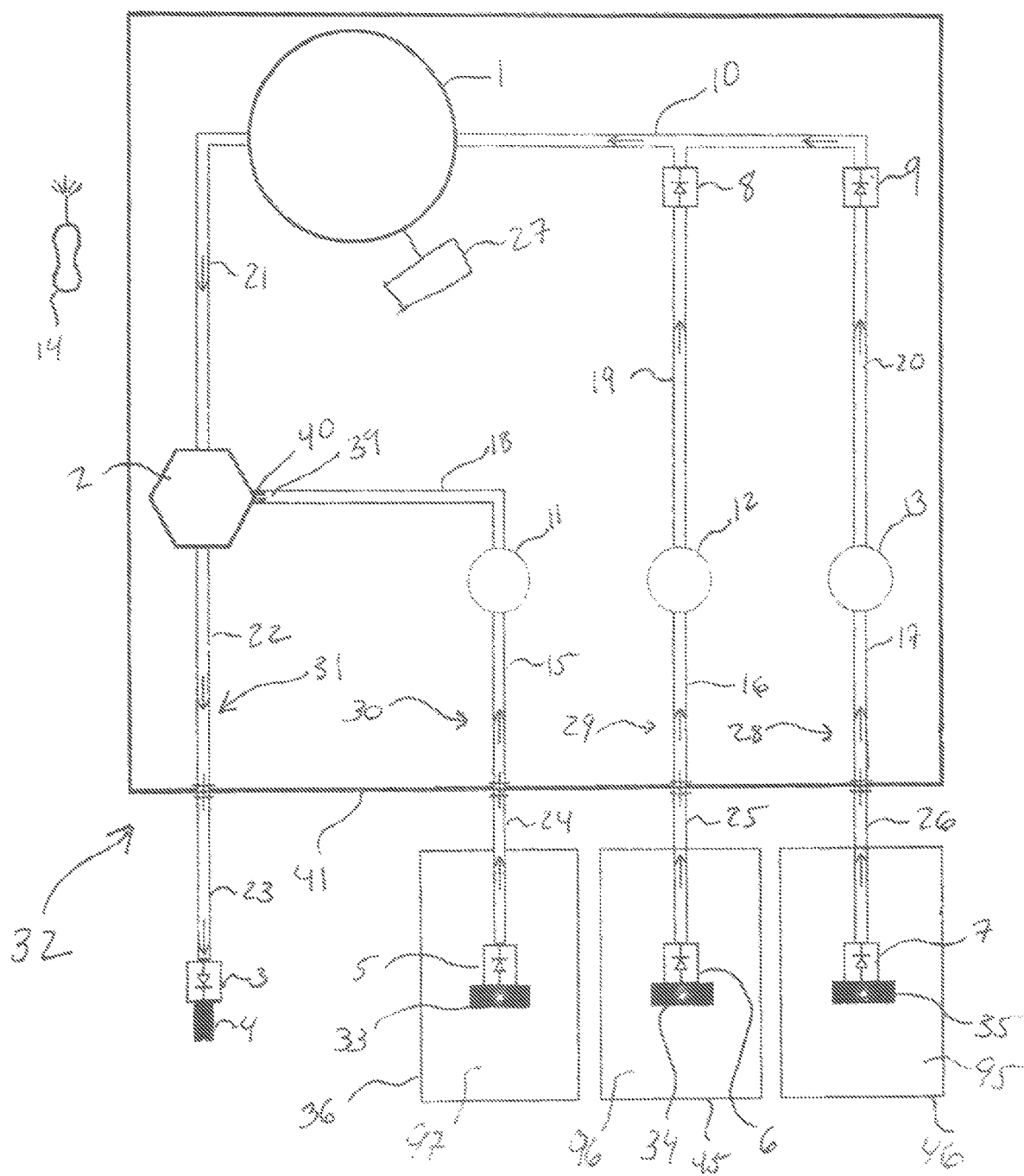
FIG. 1 illustrates an embodiment of the apparatus of the present invention where a peroxide composition, an alkaline composition and a third composition are used.

The preferred embodiment of apparatus 32 of FIG. 1 comprises a power module 27, which powers a positive displacement pump 1, as well as solenoid valves 11, 12, and 13. In a preferred embodiment, the solenoid valves 11, 12, and 13 are stainless steel, 24 volt DC and 20 watt. However, alternative solenoid valves may be used. The apparatus further comprises an alkaline input line 30, a hydrogen peroxide input line 29, an additional chemical line 28, and an output line 31.

The alkaline input line 30, further comprises chemical pick up tube 24 and composition intake line 15. The suction end of chemical pick up tube 24 further comprises an input check valve 5 with a filter screen 33. Chemical pick up tube 24 is attached to composition intake line 15, which is then attached to solenoid valve 11. Solenoid valve 11 is then attached to injector 2 by injector intake line 18. In a preferred embodiment, the injector is a Hydra-Flex Chem-Flex injector, U.S. Pat. No. 8,807,158, that is a downstream injector designed for 0.5 gallons per minute and operates on differential pressure. It is understood that alkaline input line 30 would be placed within intake reservoir 36 of the desired alkaline composition 97 such that suction of that composition could be achieved. Preferably the intake reservoir 36 and alkaline input line 30 are color coordinated to avoid confusion. Alternatively, intake reservoir 36 may comprise an organic acid.

The hydrogen peroxide input line 29, further comprises chemical pick up tube 25 and composition intake line 16. The suction end of chemical pick up tube 25 further comprises an input check valve 6 with a filter screen 34. Chemical pick up tube 25 is attached to composition intake line 16, which is then attached to solenoid valve 12. Solenoid valve 12 is then attached to pump check valve 8 by check valve line 19. It is understood that hydrogen peroxide input line 29 would be placed within a pump reservoir 45 of the desired hydrogen peroxide composition 96 such that suction of that composition could be achieved. Preferably the pump reservoir 45 and hydrogen peroxide input line 29 are color coordinated to avoid confusion.

The additional chemical input line 28, further comprises chemical pick up tube 26 and composition input line 17. The suction end of chemical pick up tube 26 further comprises an input check valve 7 with a filter screen 35. Chemical pick up tube 26 is attached to composition intake line 17, which is then attached to solenoid valve 13. Solenoid valve 13 is then attached to pump check valve 9 by check valve line 20. It is understood that additional chemical input line 28 would be placed within pump reservoir 46 of the desired additional composition 95 such that suction of that composition could be achieved. Preferably the pump reservoir 46 and additional chemical input line 28 are color coordinated to avoid confusion. In a preferred embodiment, the additional composition 95 comprises any additional chemical needed for the desired result, including, but not limited to tile and grout cleaner or a degreaser.

Pump check valves 8 and 9 are attached to pump intake line 10, which is attached to pump 1. Pump intake line 10 is preferably stainless steel. Check valves 8 and 9 prevent any back up into the check valve lines 19 and 20. Pump 1 is further attached to injector 2 by pump discharge line 21. Output line 31 comprises injector output line 22, which is attached to injector 2, and spray line 23, which is attached to output line 22. The end of spray line 23 comprises one way check valve 3 and nozzle 4. In a preferred embodiment, nozzle 4 is a stainless steel spray nozzle. Additionally, spray line 23 may comprise a wand for easier application.

Pump check valves 8 and 9 are plastic one way check valves with a crack pressure of 3 pounds. However, it is understood that alternative check valves may be used. Input check valves 5, 6 and 7 are preferably one way foot/check valves that are plastic, however other materials may be used. Check valve 3 is preferably a stainless steel one way check valve with a hastelloy spring with a crack pressure of 3 pounds. Chemical pick up tubes 24, 25, and 26, as well as lines 15-23, pump discharge line 21, and injector intake line 18 are preferably made from ethylene propylene diene monomer (EPDM) rubber, however, it is understood that alternative material may be used.

The preferred pump output of the embodiment of FIG. 1 is 0.67 gallons per minute which through injector 2 creates a pressure of 275 to 300 psi. The injector 2 is designed to operate with a 70% pressure loss across the injector 2, which when used with an appropriately sized nozzle creates an application pressure of 75 to 90 psi. A pressure gauge and voltmeter may be used to monitor the pump.

In the preferred embodiment, the power module 27 further comprises a DC power supply, terminal strips and a radio receiver. However, it is understood that any electrical equipment may be used as needed. The power module 27 is connected to a power switch (not shown) that allows the user manually start power to the apparatus and to select for the use of alkaline input line 30, hydrogen peroxide input line 29, and/or additional chemical input line 28. It is understood that any or all of the input lines may be selected based upon need. The power module 27 may be controlled from a remote transmitter 14, wherein transmitter 14 controls when power is supplied to open solenoid valves 11, 12, and 13. Transmitter 14 and/or the power switch should contain an emergency stop. Additionally, transmitter 14 may control the power switch, input selection and all other electronic components.

In the embodiment of FIG. 1, a singular feed of hydrogen peroxide may be selected by the operator. Once the power is turned on from a power switch (not shown) controlling the power module 27, the operator selects only the hydrogen peroxide feed, which controls solenoid valve 12. The selection may be made from the power switch on the apparatus 32 or the transmitter 14. Once solenoid valve 12 is open, the pump motor 1 will start. The hydrogen peroxide, 96, then flows from pump reservoir 45, through chemical pick up tube 25, through composition intake line 16, through check valve line 19, through pump check valve 8 to pump 1. The feed then travels to injector 2 at 250 to 300 psi pressure that creates a pressure drop across the injector 2 and creates suction on the downstream side of the injector 39 to injector output line 22. The flow then moves to check valve 3 to nozzle 4. Check valve 3 operates to prevent further flow once the apparatus has been turned off. The check valve 3, with a crack pressure of 3 pounds, also acts as a safety release for when the pressure in the hose and/or wand exceeds 3 pounds.

The alkaline composition, 97, may be added to the hydrogen peroxide feed. In this embodiment, the operator selects the dual feed of alkaline, 97, and hydrogen peroxide, 96. The dual feed selection will open solenoid valve 12 as described above and will also open solenoid valve 11. The alkaline composition, 97, then flows from intake reservoir 36, through the chemical pick up tube 24, through composition intake line 15, through solenoid valve 11, through injector intake line 18 and to injector 2. The alkaline composition is metered into the flow of hydrogen peroxide by a metering orifice 40 installed at the connection of injector intake line 18 and injector 2. The ratio is typically 1:20 parts hydrogen peroxide. Alternatively, when an organic acid composition is used in place of the alkaline composition 97, the organic acid composition is blended with the hydrogen peroxide composition in a ratio between 1:8 to 0.01:20.

In a further embodiment, the additional chemical composition, preferably a degreaser or tile and grout cleaner may be used. In this embodiment, solenoid valves 11 and 12 closed and solenoid valve 13 will be opened. The additional composition, 95, flows from pump reservoir 46, through chemical pick up tube 26, through composition intake line 17, through check valve line 20, through pump check valve 9, to pump 1, through pump discharge line 21 to injector 2 and through output line 31.

In a further embodiment, the apparatus 32 may be enclosed within a box 41 or panel preferably of non-corrosive metal. In such an embodiment, the power switch and selection capabilities would be placed on the exterior of the box 41. And chemical pick up tubes 24, 25, and 26, and spray line 23 would extend from the interior or the box to the exterior for ease of use.

The apparatus 32 of FIG. 1 is designed to create the chemical reaction of the alkaline and hydrogen peroxide at the point of application. Waste and heat buildup are minimized by creating a reaction on when needed.

Figure 2:
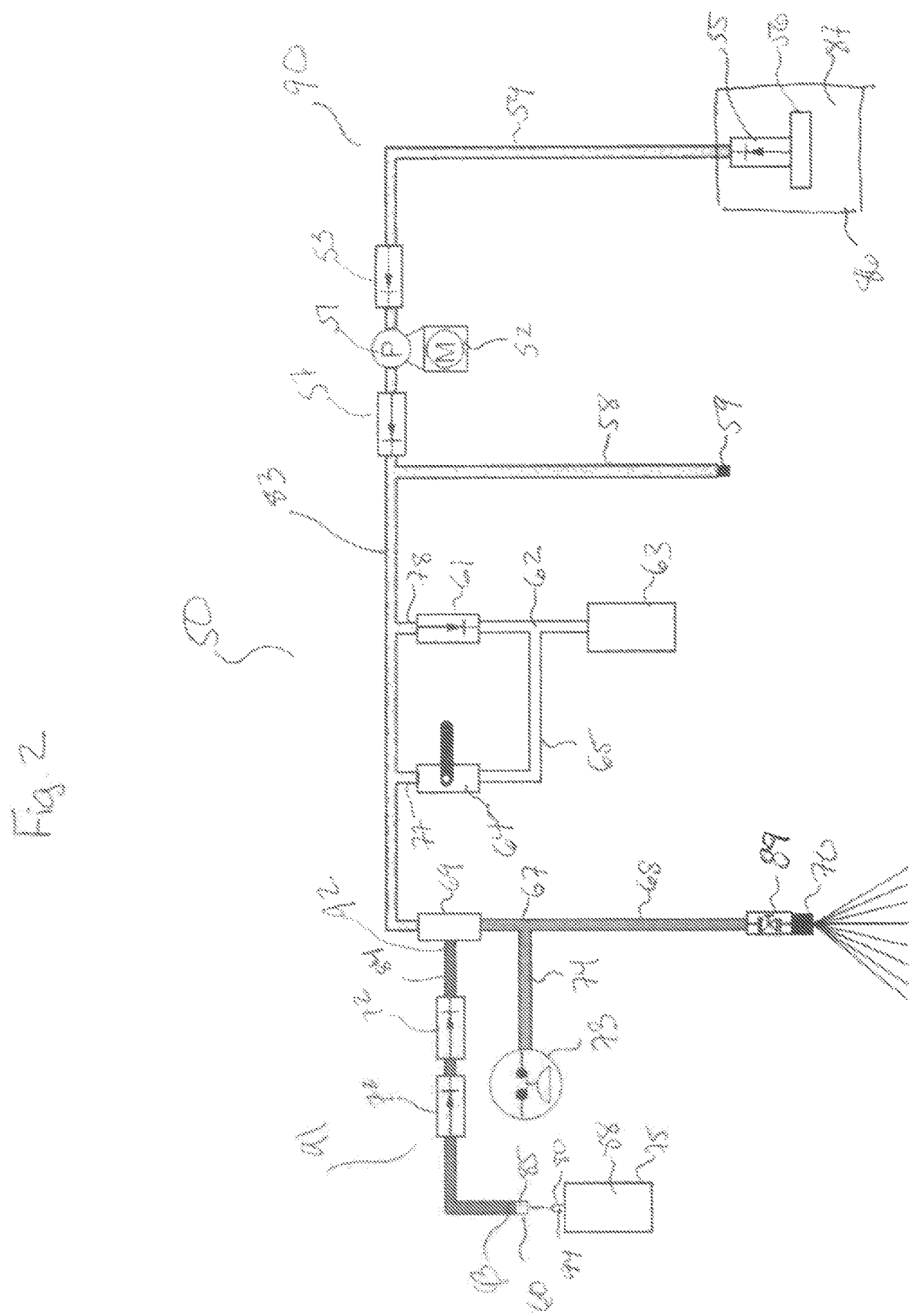
FIG. 2 illustrates an embodiment of the apparatus of the present invention wherein a peroxide composition and an alkaline composition are used.

The preferred embodiment of apparatus 50 shown in FIG. 2 comprises a motor 52 that powers pump 51, preferably a positive displacement pump. The apparatus further comprises an injector reservoir 75 containing an alkaline 88 and a pump reservoir 86 containing a hydrogen peroxide composition 87.

In the embodiment shown in FIG. 2, there is one pump check valve system 90. Alternatively, there may be several pump check valve systems. Each pump check valve system consists of a pump reservoir 86, a pump intake check valve 53, and a composition pick up tube 54. The pump reservoir further consists of filter 56 and check valve 55, alternatively, filter 56 and check valve 55 may be one unit, or a foot valve. Alternatively, filter 56 and check valve 55 may be located on the outside or within pump reservoir 86. Check valve 55 is connected to composition pick up tube 54. Composition pick up tube 54 is connected to pump 51. In a preferred embodiment, a check valve 53 is placed on the composition pick up tube 54 prior to the hydrogen peroxide feed entering pump 51.

The hydrogen peroxide composition 87 flows from pump 51 into pump discharge line 83. In a preferred embodiment, a pulsation dampener 58, to smooth the pulses of the pump, is connected to pump outlet line 83. The pulsation dampener 58 further consists of a plug 59. A pump output check valve 57 is located in between the pump 51 and the pulsation dampener 58. A waste bottle line 78 is connected to pump output line 83 and waste bottle 63. Waste bottle line 78 consists of a waste bottle check valve 61 and a T-connector 62. Downstream from the waste bottle line 78, a ball valve input line 77 is connected to pump output line 83 and ball valve 64. Ball valve output line 65 connects ball valve 64 with T-connector 62. Ball valve 64 may be used to back wash injector 69.

Downstream from ball valve input line 77, pump output line 83 is connected to injector 69. Injector 69 is connected to alkaline input line 84 and output line 68.

As shown in FIG. 2, the apparatus 50 contains at least one injector intake system 91. Each injector intake system 91 consists of an injector reservoir 75 that contains alkaline composition 88. Injector reservoir 75 is connected to injector input line 84 by injector cap 60. The injector cap 60 contains injector cap check valve 85, which may contain a filter (not shown). Injector reservoir 75 may contain a reservoir cap 80, which is where the reservoir attaches the injector cap check valve 85. The reservoir cap 80 may contain a reservoir check valve 94, wherein reservoir check valve 94 and/or reservoir cap 80, and injector cap check valve 85 can be screwed together or otherwise attached. Alternatively, reservoir check valve 94 may be placed directly in the injector reservoir 75. Downstream from injector reservoir 75, two injector check valves 72 are located on injector input line 84 in between the injector end 92 and the reservoir end 93.

Pressure switch 73 is connected to output 68 at t-connection 67 by pressure connection 74. Downstream from t-connection 67, trigger check valve 89 is connected to output line 68. Trigger check valve 89 is then connected to nozzle 70.

I claim:

1. An apparatus for supplying a peroxide composition and an alkaline composition simultaneously for removal and destruction of microbiological and organic contamination on a surface comprising:
   a motor;
   a pump connected to the motor;
   a pump intake line, wherein one end of the pump intake line is connected to the pump and the other end is connected to at least one pump check valve system, wherein each pump check valve system further comprises:
      a pump check valve, wherein the check valve is connected to the pump intake line,
      a composition pick up tube, wherein the composition pick up tube is connected to the pump check valve and an intake check valve, and the intake check valve is connected to a filter screen, wherein the intake check valve and filter screen are within a reservoir, wherein the reservoir of at least one pump valve system contains hydrogen peroxide;

a pump discharge line connected to the pump;

an injector connected to the pump discharge line;

an injector intake system, wherein the injector intake system is independent of the pump intake line and the at least one pump check valve system, and the injector intake system further comprises:

> an injector input line, comprising a first end and a second end, wherein the first end is connected to the injector and the second end is attached to an injector cap check valve,
>
> at least one injector check valve, wherein each injector check valve is connected to the injector input line in between the first and second end of the injector input line,
>
> an injector reservoir, wherein the injector reservoir contains an alkaline composition and comprises a reservoir check valve that is connected to the injector cap check valve;

an output line, wherein the output line is connected to the injector and a trigger check valve, and the trigger check valve is attached to the output line upstream of a handheld spray nozzle; and a pressure switch, wherein the pressure switch is connected to the output line by a pressure line in between the injector and the trigger check valve.

2. The apparatus of claim 1, wherein a pulsation dampener is connected to the pump discharge line.

3. The apparatus of claim 1, wherein a pump output check valve is connected to the pump discharge line in between the pump and the injector.

\* \* \* \* \*